United States Patent [19]
Kuroda et al.

[11] Patent Number: 6,129,681
[45] Date of Patent: *Oct. 10, 2000

[54] APPARATUS AND METHOD FOR ANALYZING INFORMATION RELATING TO PHYSICAL AND MENTAL CONDITION

[75] Inventors: Yukio Kuroda, Toyota; Tomoyuki Yoshida, Tsuchiura, both of Japan

[73] Assignees: Toyota Jidosha Kabushiki Kaisha, Toyota; Agency of Industrial Science & Technology-Director-General, Tokyo, both of Japan

[*] Notice: This patent is subject to a terminal disclaimer.

[21] Appl. No.: 08/934,595

[22] Filed: Sep. 22, 1997

Related U.S. Application Data

[63] Continuation of application No. 08/521,810, Aug. 31, 1995, Pat. No. 5,884,626.

[30] Foreign Application Priority Data

Sep. 2, 1994 [JP] Japan ..................................... 6-210064
Jul. 31, 1995 [JP] Japan ..................................... 7-194895

[51] Int. Cl.$^7$ ...................................................... A61B 5/00
[52] U.S. Cl. .......................................... 600/544; 600/300
[58] Field of Search ..................................... 600/544, 545, 600/300

[56] References Cited

U.S. PATENT DOCUMENTS

| | | |
|---|---|---|
| 4,862,359 | 8/1989 | Trivedi et al. ........................... 600/544 |
| 5,325,862 | 7/1994 | Lewis et al. . |
| 5,447,166 | 9/1995 | Gevins ..................................... 600/544 |
| 5,522,863 | 6/1996 | Spano et al. ............................ 600/544 |
| 5,601,090 | 2/1997 | Musha ..................................... 600/544 |
| 5,813,993 | 9/1998 | Kaplan et al. ........................... 600/544 |

FOREIGN PATENT DOCUMENTS

A 0 551 524  7/1993  European Pat. Off. .
A 0 555 591  8/1993  European Pat. Off. .

*Primary Examiner*—Robert L. Nasser
*Attorney, Agent, or Firm*—Oliff & Berridge, PLC

[57] ABSTRACT

An apparatus and method are provided for analyzing information relating to the physiological and psychological conditions of a driver. Psychological conditions such as comfortableness or degree of alertness are estimated on the basis of physical data such as fluctuation in brain waves. This apparatus comprises a first neural network having a pre-processed 1/f fluctuation signal for brain waves as an input and for estimating a degree of alertness of the driver, and a second neural network receiving the estimated degree of alertness and the pre-processed 1/f fluctuation signal, for estimating and outputting driving comfortableness. By employing a neural network, which has a mapping ability as well as flexible adaptability even for non-linear data, based on the learning function, more accurate estimation of mental conditions can be achieved in comparison with conventional statistical analysis.

14 Claims, 17 Drawing Sheets

BRAIN ANATOMY

|  | ALERTNESS | COMFORTABLE-NESS | EEG FLUCTUATION COEFFICIENT | | | | | | | |
|---|---|---|---|---|---|---|---|---|---|---|
| SUBJECT | ALERT | COMF | F3 | F4 | C3 | C4 | P3 | P4 | O1 | O2 |
| 1 | 0.550 | 0.500 | -0.560 | -0.497 | -0.523 | -0.588 | -0.597 | -0.536 | -0.461 | -0.723 |
| 2 | 0.350 | 0.500 | -0.719 | -0.697 | -0.805 | -0.756 | -0.877 | -0.930 | -0.906 | -0.916 |
| 3 | 0.550 | 0.550 | -0.667 | -0.325 | -0.553 | -0.553 | -0.806 | -0.702 | -0.631 | -0.740 |
| 4 | 0.500 | 0.550 | -0.429 | -0.285 | -0.700 | -0.631 | -0.686 | -0.778 | -0.630 | -0.628 |
| 5 | 0.750 | 0.875 | -0.686 | -0.339 | -0.921 | -0.859 | -0.708 | -0.937 | -0.814 | -1.292 |
| 6 | 0.650 | 0.250 | -0.413 | -0.277 | -0.627 | -0.425 | -0.454 | -0.598 | -0.490 | -0.685 |
| 7 | 0.700 | 0.725 | -0.450 | -0.462 | -0.504 | -0.511 | -0.523 | -0.561 | -0.836 | -0.716 |
| 8 | 0.850 | 0.800 | -0.182 | -0.539 | -0.320 | -0.431 | -0.401 | -0.630 | -0.482 | -0.467 |
| 9 | 0.250 | 0.550 | -0.264 | -0.140 | -0.336 | -0.299 | -0.192 | -0.219 | -0.278 | -0.210 |
| 10 | 0.550 | 0.500 | -0.497 | -0.423 | -0.349 | -0.347 | -0.257 | -0.275 | -0.383 | -0.601 |
| 11 | 0.600 | 0.800 | -0.440 | -0.300 | -0.527 | -0.502 | -0.591 | -0.539 | -0.473 | -0.504 |
| 12 | 0.500 | 0.500 | -0.414 | -0.353 | -0.417 | -0.594 | -0.364 | -0.489 | -0.643 | -0.580 |
| 13 | 0.500 | 0.350 | -0.673 | -0.750 | -0.650 | -0.828 | -0.393 | -0.575 | -0.724 | -0.681 |
| 14 | 0.250 | 0.500 | -0.741 | -0.779 | -0.987 | -0.813 | -0.888 | -0.816 | -0.740 | -1.030 |
| 15 | 0.325 | 0.350 | -0.353 | -0.115 | -0.364 | -0.179 | -0.407 | -0.018 | -0.309 | -0.193 |
| 16 | 0.350 | 0.700 | -0.137 | -0.586 | -0.556 | -0.583 | -0.432 | -0.459 | -0.261 | -0.079 |
| 17 | 0.800 | 0.800 | -0.598 | -0.541 | -0.699 | -0.487 | -0.715 | -0.705 | -0.663 | -0.756 |
| 18 | 0.100 | 0.500 | -0.726 | -0.716 | -0.559 | -0.421 | -0.478 | -0.568 | -0.631 | -0.707 |
| 19 | 0.350 | 0.550 | -0.699 | -0.619 | -0.649 | -0.613 | -0.630 | -0.712 | -0.731 | -0.720 |
| 20 | 0.450 | 0.600 | -0.684 | -0.455 | -0.418 | -0.264 | -0.557 | -0.371 | -0.666 | -0.436 |
| 21 | 0.300 | 0.650 | -0.498 | -0.423 | -0.510 | -0.458 | -0.419 | -0.560 | -0.361 | -0.459 |
| 22 | 0.400 | 0.700 | -0.367 | -0.011 | -0.256 | -0.307 | -0.119 | -0.003 | -0.073 | -0.237 |
| 23 | 0.750 | 0.750 | -0.934 | -0.879 | -0.968 | -0.972 | -0.833 | -0.818 | -0.833 | -0.907 |
| 24 | 0.500 | 0.500 | -0.331 | -0.460 | -0.364 | -0.361 | -0.318 | -0.034 | -0.168 | -0.091 |
| 25 | 0.625 | 0.650 | -0.420 | -0.274 | -0.384 | -0.429 | -0.479 | -0.425 | -0.318 | -0.206 |
| 26 | 0.500 | 0.500 | -0.290 | -0.216 | -0.490 | -0.140 | -0.293 | -0.347 | -0.392 | -0.095 |
| 27 | 0.800 | 0.800 | -0.902 | -0.899 | -0.837 | -0.785 | -0.783 | -0.669 | -0.728 | -0.780 |
| 28 | 0.800 | 0.825 | -0.720 | -0.887 | -0.656 | -0.723 | -0.735 | -0.693 | -0.553 | -0.674 |
| 29 | 0.825 | 0.825 | -0.457 | -0.483 | -0.469 | -0.545 | -0.674 | -0.525 | -0.513 | -0.395 |
| 30 | 0.825 | 0.850 | -0.570 | -0.626 | -0.545 | -0.642 | -0.766 | -0.617 | -0.565 | -0.592 |
| 31 | 0.050 | 0.750 | -0.615 | -0.622 | -0.724 | -0.607 | -0.804 | -0.717 | -0.768 | -0.767 |
| 32 | • | • | • | • | • | • | • | • | • | • |
| 33 | • | • | • | • | • | • | • | • | • | • |

EXPERIMENTAL DATA

Fig. 3

(A) EEG FLUCTUATION → ALERTNESS ESTIMATION NN TEMPLATE
(NN alertness)

(B) EEG FLUCTUATION +ALERTNESS → COMFORTABLENESS ESTIMATION NN TEMPLATE (NN comf)

(A) EEG FLUCTUATION → COMFORTABLENESS ESTIMATION NN TEMPLATE (B) EEG FLUCTUATION → ALERTNESS + COMFORTABLENESS ESTIMATION NN TEMPLATE

EXPERIMENT RESULT OF ALERTNESS ESTIMATION NN
(THE NUMBER OF HIDDEN UNITS = 35)

EXPERIMENT RESULT OF ALERTNESS ESTIMATION NN
(THE NUMBER OF HIDDEN UNITS = 35)

· TRAINING DATA (1,100 PATTERNS) AND NN ESTIMATED VALUE    { · ~ TRAINING DATA
O ~ NN ESTIMATED VALUE }

EXPERIMENT RESULT OF ALERTNESS ESTIMATION NN
(THE NUMBER OF HIDDEN UNITS = 70)

· TEST DATA (100 PATTERNS) AND NN ESTIMATED VALUE

{ · ~ TEST DATA
O ~ NN ESTIMATED VALUE }

EXPERIMENT RESULT OF ALERTNESS ESTIMATION NN
(THE NUMBER OF HIDDEN UNITS = 70)

• TRAINING DATA (1,100 PATTERNS) AND NN ESTIMATED VALUE

• TEST DATA (100 PATTERNS) AND NN ESTIMATED VALUE

CORRELATION BETWEEN EXPERIMENTAL DATA (1,200 DATA)

|  | F3 | F4 | C3 | C4 | P3 | P4 | O1 | O2 | ALERT | CONF |
|---|---|---|---|---|---|---|---|---|---|---|
| F3 | 1.000 | 0.763 | 0.744 | 0.653 | 0.640 | 0.642 | 0.562 | 0.519 | 0.158 | 0.000 |
| F4 | 0.763 | 1.000 | 0.701 | 0.703 | 0.640 | 0.612 | 0.539 | 0.484 | 0.105 | 0.000 |
| C3 | 0.744 | 0.701 | 1.000 | 0.707 | 0.717 | 0.675 | 0.561 | 0.515 | 0.164 | 0.000 |
| C4 | 0.653 | 0.703 | 0.707 | 1.000 | 0.657 | 0.659 | 0.525 | 0.494 | 0.122 | 0.032 |
| P3 | 0.640 | 0.640 | 0.717 | 0.657 | 1.000 | 0.772 | 0.601 | 0.581 | 0.158 | 0.032 |
| P4 | 0.642 | 0.612 | 0.675 | 0.659 | 0.772 | 1.000 | 0.593 | 0.595 | 0.210 | 0.000 |
| O1 | 0.562 | 0.539 | 0.561 | 0.525 | 0.601 | 0.593 | 1.000 | 0.744 | 0.212 | 0.000 |
| O2 | 0.519 | 0.484 | 0.515 | 0.494 | 0.581 | 0.595 | 0.744 | 1.000 | 0.202 | 0.000 |
| ALERT | 0.158 | 0.105 | 0.164 | 0.122 | 0.158 | 0.210 | 0.212 | 0.202 | 1.000 | 0.217 |
| COMF | 0.000 | 0.000 | 0.000 | 0.032 | 0.032 | 0.000 | 0.000 | 0.000 | 0.217 | 1.000 |

{ ALERT~ALERTNESS
COMF~CONFORTABLENESS }

Fig. 10

EXPERIMENTAL CONDITIONS FOR ALERTNESS ESTIMATION NN
AND THE RESULTS

| THE NUMBER OF HIDDEN UNITS | THE NUMBER OF TRAINING ACTIONS | TRAINING ERROR | TEST ERROR | INPUT-OUTPUT RELATION ON DOMINANT PORTION | RESULT |
|---|---|---|---|---|---|
| 35 | $5 \times 10^8$ | 11.8% | 19.6% | P4(20.9%)<br>C3(19.9%) | Fig. 7A<br>Fig. 7B |
| 70 | $6 \times 10^8$ | 11.5% | 19.3% | C4(27.2%)<br>P4(14.3%) | Fig. 8A<br>Fig. 8B |

Fig. 11

EXPERIMENTAL CONDITIONS FOR COMFORTABLENESS ESTIMATION NN AND THE RESULTS

| THE NUMBER OF HIDDEN UNITS | THE NUMBER OF TRAINING ACTIONS | TRAINING ERROR | TEST ERROR | INPUT-OUTPUT RELATION ON DOMINANT PORTION | RESULT |
|---|---|---|---|---|---|
| 70 | $3 \times 10^8$ | 10.0% | 20.4% | F3(21.3%) C3(17.5%) | Fig. 9A Fig. 9B |

Fig. 12

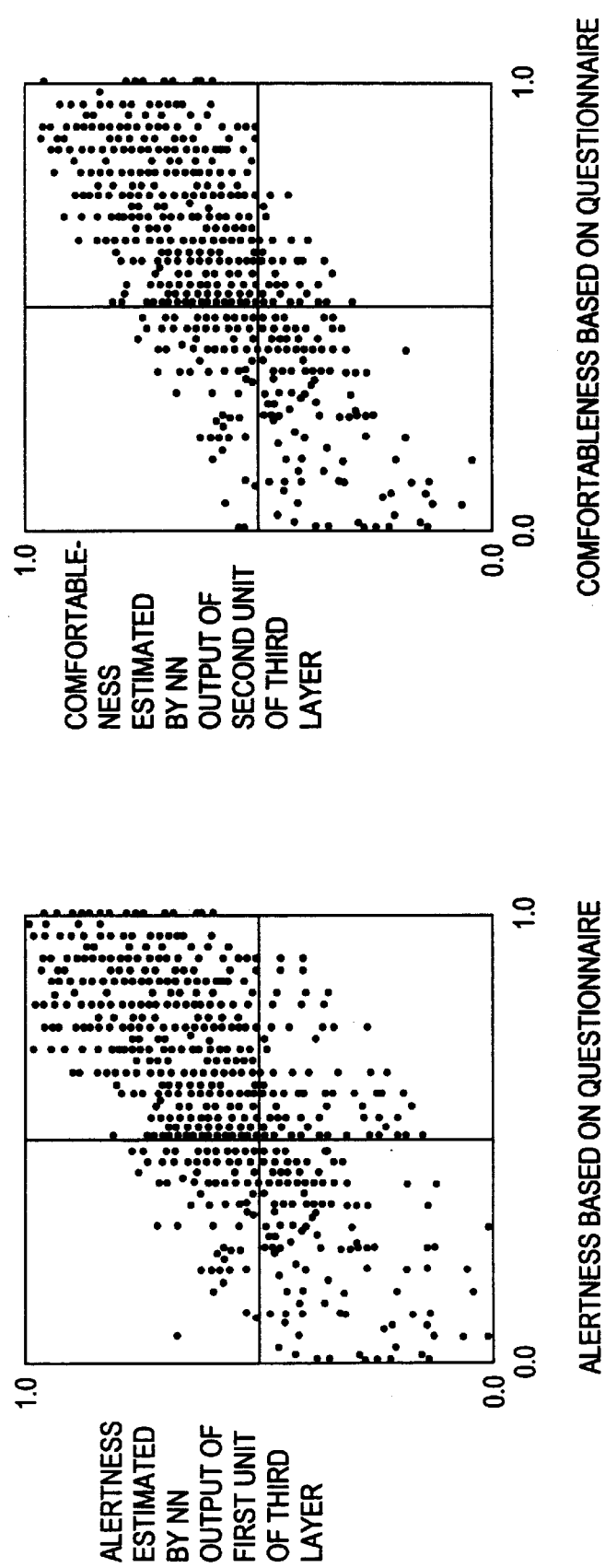

Comfortableness is mostly recognizable, and there is not so big difference between the actual comfortableness of the subject and psychological evaluation obtained by a questionnaire.
On the other hand, alertness or degree of fatigue is often non-recognizable, and actual work result can be a better indication of the psychological condition of the subject rather than the questionnaire results.

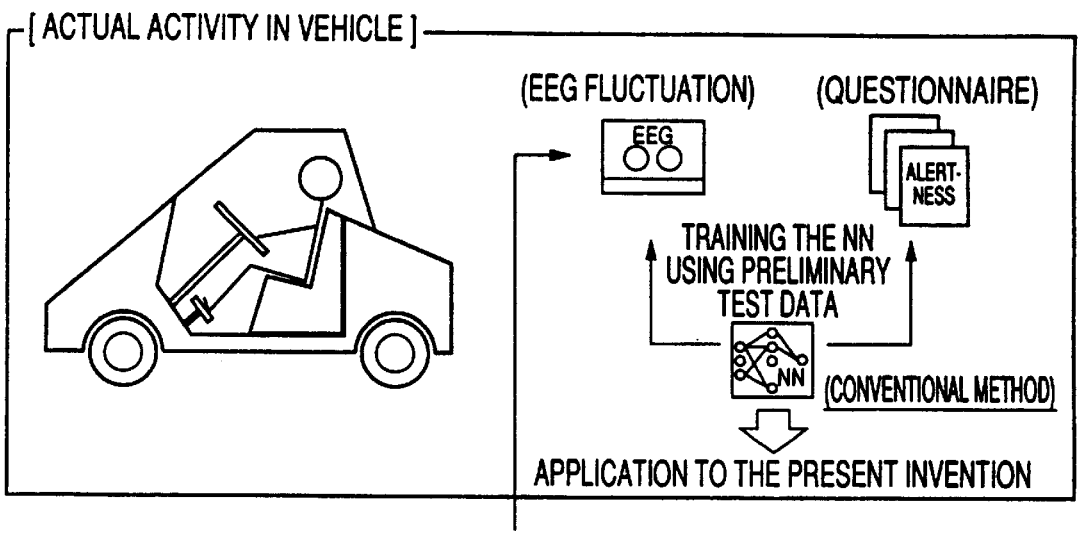

Applying the Relation between the EEG Fluctuation and Alertness (or Comfortableness) Obtained by Experiment to the Trained NN and Actual Work

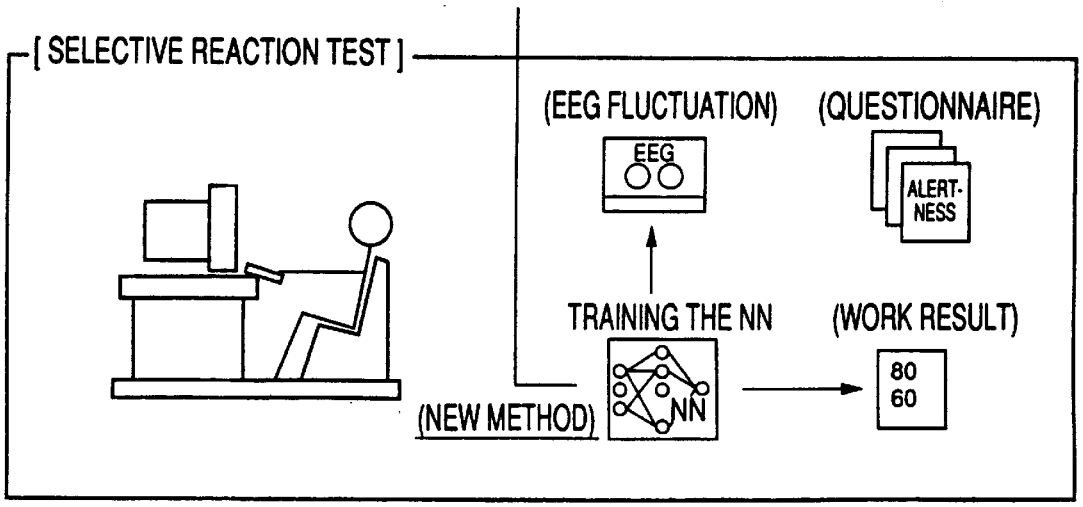

Fig. 17

APPARATUS AND METHOD FOR ANALYZING INFORMATION RELATING TO PHYSICAL AND MENTAL CONDITION

This appln. is a con't of Ser. No. 08/521,810, filed Aug. 31, 1995, now U.S. Pat. No. 5,884,626.

BACKGROUND OF THE INVENTION

1. Field of the Invention

This invention generally relates to an apparatus and method for analyzing information concerning the physical and mental condition of a person, and more particularly to an apparatus and method for relating physical data (physiological factors) such as brain waves with mental data (psychological factors) such as alertness (wakefulness) or comfortableness (pleasantness).

2. Description of the Prior Art

People nowadays have many diversified views concerning their residence, work environment, and vehicles. The basis of selecting such things is being shifted from "on function" to "on human characteristics". As importance is thus increasingly attached to human sensitivity, a growing number of studies has recently begun to focus on sensitivity, or comfortableness.

Comfortableness stems from human feeling closely related to living conditions. The fact that feeling is subjective makes it difficult to measure by objective methods. Thus most evaluations for comfortableness have been qualitative and based on sensation, and there is virtually no established method of measuring it quantitatively.

As a quantitative analysis of human information, many studies for associating physical data such as brain waves, electrodiagrams, or heartbeat data with mental data such as alertness or comfortableness have been conducted. These attempts intend to more accurately estimate mental (psychological) data such as alertness and comfortableness quantitatively on the basis of physical data. Techniques of finding correlation between physiological factors and psychological factors generally utilize statistical analysis including multiple regression analysis and analysis of variance so as to develop an algorithm for estimating psychological data based on the analysis results. However, no useful algorithm has been developed yet which is sufficiently accurate and universal for practical use.

SUMMARY OF THE INVENTION

Physical and mental information inherently contain non-linear and vague characteristics. Accordingly, statistic analysis, which is basically a linear method, using such data inevitably involves problems. Since probabilities based on quantitative measurement of feeling are required for the design of products or space offering comfortableness, objective measurement and evaluation of feeling has been strongly sought after.

In view of these demands, the inventors have developed a study of measurement using EEG fluctuation (i.e. 1/f fluctuation in brain waves) as an indicator and estimation through the use of a neural network (hereinafter NN). Focusing on a neural network's non-linear mapping ability and adaptability based on learning functions, the inventors utilized a neural network to develop an efficient algorithm for estimating mental data from physical data, and have established a technique of quantitatively measuring such mental data (e.g. degree of comfortableness). Thus, the object of the invention is to provide an apparatus and method for estimating mental (or psychological) data based on physical (or physiological) data such as brain waves.

In order to achieve the object, an apparatus for analyzing information relating to physical and mental conditions in accordance with the invention comprises a neural network receiving a physiological fluctuation signal as an input and for estimating mental (or psychological) conditions based on the physiological fluctuation signal. It is known that a physiological fluctuation signal has a close relation with the psychological conditions of a human being, and good estimation of psychological conditions is achieved by using such a physiological fluctuation signal.

The physiological fluctuation signal may be an EEG fluctuation which has been pre-processed. It is known that brain waves are closely associated with psychological conditions of a human being, and the psychological condition can be satisfactorily estimated from the pre-processed EEG fluctuation signal.

The psychological conditions include degree of alertness. Alertness is a basic element of psychological conditions, and measurement of alertness leads to good estimation of psychological conditions of a human being.

The psychological conditions further include comfortableness. Measurement of comfortableness also leads to preferable quantitative estimation of psychological conditions.

The neural network comprises a first neural network having a pre-processed EEG fluctuation signal as an input, for estimating alertness, and a second neural network having the pre-processed EEG fluctuation signal and alertness estimated by the first neural network as inputs, for estimating comfortableness. In this example, degree of alertness and comfortableness are obtained for estimating psychological conditions. Especially, degree of alertness estimated by the first neural network is input to the second neural network to further estimate comfortableness. It is known that comfortableness strongly depends on the degree of alertness, and thus, comfortableness can be estimated more accurately by inputting the alertness as a parameter into the second network in the above-mentioned structure.

In another aspect of the invention, there is provided a method for analyzing physical and mental information. This method comprises the steps of inputting a physiological fluctuation signal to a neural network, and estimating psychological conditions based on the physiological fluctuation signal.

The physiological fluctuation signal includes an EEG fluctuation signal.

The psychological conditions include degree of alertness and comfortableness.

This method further comprises the steps of applying the EEG fluctuation signal to a first neural network to estimate alertness, and inputting both the EEG fluctuation signal and the value of alertness obtained by the first neural network to a second neural network to further estimate comfortableness. In this case, both alertness and comfortableness are used for estimation of psychological conditions.

In the above-mentioned aspects of the invention, psychological evaluations based on questionnaire surveys are supplied as teacher signals to the neural network. However, it is more preferable to train the neural network, rather than using questionnaire results as main parameters, because psychological evaluation obtained by questionnaire generally contains differences among individuals. For this reason, an hourglass type of neural network is used, in which EEG fluctuation signals are supplied both as input and output for training the neural network. Internal expressions corresponding to psychological conditions are obtained in the intermediate layers of the hourglass type neural network through the learning of the network.

In one example of the invention, the neural network is an hourglass type of neural network having intermediate layers between input and output for learning. Both the input and output of the network are EEG fluctuation signals. Outputs of the intermediate layers represent a psychological condition. The training of the network using only EEG fluctuation signals, without relying on questionnaire-based evaluation, achieves more accurate estimation of psychological conditions.

In the case of combining first and second neural networks for estimating alertness and comfortableness, respectively, both neural networks are hourglass type neural networks. Output values of the intermediate layers of each neural network represent psychological conditions.

Use of hourglass type neural networks can apply to the method for analyzing physical and mental information.

Although, EEG fluctuation signals are used as physical data for the purpose of estimating psychological conditions, it is applicable to the estimation of working achievement, because alertness has a close relation with the working result.

BRIEF DESCRIPTION OF THE DRAWINGS

FIG. 3 is a table showing experimental data.

FIG. 10 shows a correlation between the experimental data.

FIG. 11 shows experimental conditions and results for the alertness estimating NN.

FIG. 12 shows experimental conditions and results for the comfortableness estimating NN.

FIGS. 16A and 16B show graphs plotting the relationship between output values of the first and second unit in the third layer of the hourglass type of neural network shown in FIG. 15, and alertness and comfortableness obtained by questionnaire survey, respectively.

FIG. 17 illustrates a principle of obtaining degree of alertness and comfortableness of the driver based on actual work results.

DESCRIPTION OF PREFERRED EMBODIMENT

Figure 1:
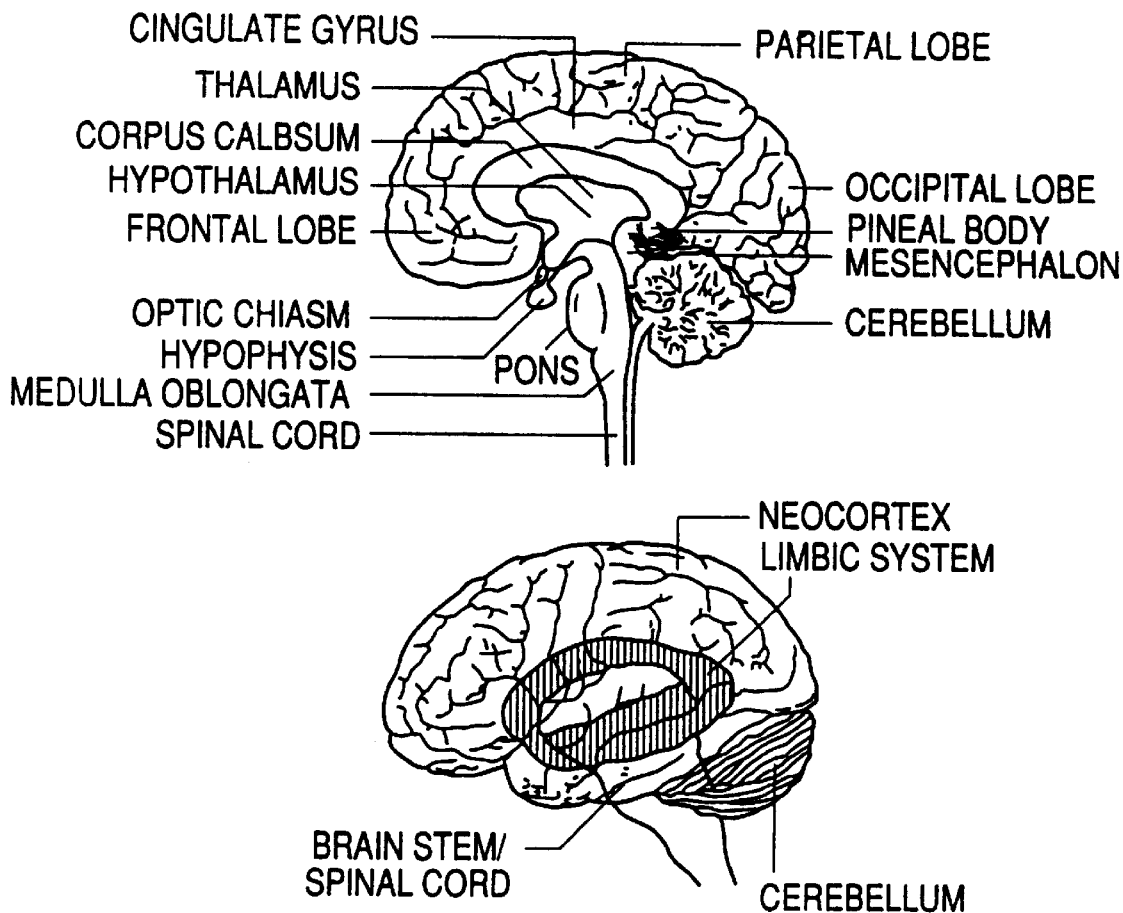
FIG. 1 illustrates the structure of a human brain.

The principle of the invention will now be described referring to the actual results of estimation of psychological conditions from EEG fluctuation.

A. MEASURING METHOD OF ALERTNESS AND COMFORTABLENESS USING FREQUENCY FLUCTUATION OF α-WAVE AS AN INDICATOR

One example of quantitative measurement of feeling is measurement using fluctuation characteristics in α-wave as a parameter.

Brain waves detected through the scalp are represented as a voltage change of around 50 $\mu$V having a frequency component of around 60 Hz. In experimentation for adults, a frequency component of 8–13 Hz is dominantly observed while resting with their eyes closed or during relaxation. This frequency component is called α-waves. Waves of around 10 Hz appear most frequently, but do not always appear at a constant cycle, as is seen from that fact the average range is 8–13 Hz. The frequency speed is increased or decreased as time elapses.

A-1. 1/f Fluctuation and Comfortableness

When representing a fluctuation spectrum on the double logarithmic scale with the vertical axis for fluctuation (power value) and the horizontal axis for the fluctuation frequency, the power value decreases in reverse proportion to frequency f with a gradient −1 as the frequency increases. The fluctuation having this characteristic is defined as a 1/f fluctuation. Returning the fluctuation characteristics thus obtained to the time axis gives the auto-correlation function of the fluctuation. The 1/f fluctuation, originally discovered as a physical fluctuation such as heat noise, does not have the same characteristics as white noise fluctuation which has no correlation with the past fluctuation information, but does keep a certain degree of correlation with the past fluctuation as seen in the Markov linkage.

1/f fluctuation has been incorporated into recent home electrical appliances and automobile air-conditioners, where it is implicitly assumed that anything with 1/f fluctuation occurring as time elapses will produce a feeling of tranquility. Such an assumption is considered to have originated in research which has revealed that, as a result of spectrum analysis, breeze flows, rivulet sounds, and classical music rhythms have 1/f fluctuation and that electrical stimulus with 1/f fluctuation is effective in removing pain. Many problems remain to be studied, however, such as the relationship between stimuli with 1/f fluctuation and biorhythm and psychological conditions including feeling.

A-2. Logical Background of Analysis of Fluctuation Phenomenon

Generally, an autocorrelation function and a power spectrum density function are used for analysis of statistical characteristics of the fluctuation phenomenon. Assuming that an irregular variable for time "t" is x(t) and a variable for time "t+τ" (τ time period later than time t) is x(t+τ), the autocorrelation function is defined by a time average value of multiplication of these two variables. This is represented by the following expression.

$$C(\tau) = \lim_{T \to \infty} \frac{1}{2} \int_{-T}^{T} \chi(t) \cdot \chi(t+\tau) dt \quad (1)$$

The above formula (1) is a function of only τ, regardless of time t. It is known that, for the formula (1), when the fluctuation is completely random, the following expression is effected.

$C(\tau)=0 (\tau \neq 0)$ $C(\tau)=C(0)(\tau=0) \quad (2)$

The noise having the autocorrelation value zero, when lag τ≠0 is defined as white noise. The autocorrelation function is an even function which has the maximum value when τ=0. This is expressed by the following expression.

$C(0) > \pm C(\tau)(\tau \neq 0) \quad (3)$

Most fluctuations maintain the previous characteristics even after micro lag time Δt to some extent. This is because of the fact that, for such fluctuations, the value at a time "t" strongly correlates with a value at time very close to "t" and the correlation becomes lower with a value at a time apart from "t". The correlation decreases exponentially as the value τ increases, and finally becomes C(τ)=0. In other words, such a fluctuation has characteristics expressed as C(τ)→0 (τ→∞). Assuming that the lag τ satisfying the equation C(τ)=0 is $\tau_0$, C(τ) is expressed as follows.

$$C(\tau) = \overline{V^2} e - (|\tau|/\tau_0) \quad (4)$$
$$(C(0) = \overline{V^2})$$

In this case, the larger the lag $\tau_0$, the slower the rate of decrease of C(τ), which is depicted as a shape widening toward the bottom.

On the other hand, power spectrum P(f) is associated with the autocorrelation function, as expressed below, in accordance with Wiener-Khintchine's formula.

$$P(f) = 4 \int_0^\infty C(\tau) \cos 2\pi f \tau d\tau \quad (5)$$

-continued
$$C(\tau) = 2 \int_0^\infty P(f) \cos 2\pi f \tau df \quad (6)$$

When incorporating the equation (5) into the equation (6), the following equation can be obtained.

$$P(f) = 4 \int_0^\infty \overline{V^2} e^{-(|\tau|/\tau_0)} \cos 2\pi f \tau d\tau \quad (7)$$
$$= 4\tau_0 \overline{V^2} / \{1 + (2\pi f \tau_0)\}^2$$

In the equation (7), if frequency f corresponding to the lag τ is much smaller than $1/2\pi\tau_0$ (that is, $1/2\pi\tau_0 \gg f$, which means $1 \gg 2\pi f\tau_0$), the value $(2\pi f\tau_0)^2$ can be almost ignored and P(f) has a constant value $f_0$ regardless of frequency. On the other hand, if "f" is much larger than $1/2\pi\tau_0$ (that is, $1/2\pi\tau_0 \ll f$, which means $1 \ll 2\pi f\tau_0$), the value of P(f) shown in the equation (5) varies depending on the value $(2\pi f\tau_0)^2$.

Therefore, in the frequency band of $1/2\pi\tau_0 \ll f$, P(f) varies in accordance with $f^{-2}$ and the power spectrum rapidly decreases as frequency increases. The fact that P(f) varies with a negative gradient with respect to frequency f means that the influence of x(t) remains until time $\tau_0$. In the case that P(f) is in proportion to $f^{-1}$ (i.e. 1/f), the smaller the negative gradient, the higher the degree of randomness. In other words, when the negative gradient is sharp, the power spectrum exhibits a slow variation. A 1/f fluctuation is located in the middle of these two, which indicates that P(f) is approximately in proportion to $f^{-1}$.

B. EVALUATION METHOD FOR PHYSIOLOGICAL AND PSYCHOLOGICAL MEASUREMENT OF COMFORTABLENESS

B-1. Significance of EEG Fluctuation as a Physiological Indicator of Comfortableness Physiological responses, which are readily and non-invasively observed and have been conventionally used, include (i) central responses such as spontaneous brain waves, sensory evoked potential, or event-related potential, (ii) peripheral response such as heart beat, pulse rate, breathing rate, or body temperature, and (iii) motor responses such as eye movement, blinking or myogenic potential. Central responses have such disadvantages that they need laborious measurement and analysis, while peripheral responses have a disadvantage that they are subject to ceiling effects for maintaining the function of a living body in spite of simple measurement. It is therefore preferable to conduct multi-faceted measurement including peripheral responses, but centering on brain activities (such as brain waves and brain electromagnetic waves).

The human brain consists of the two cerebral hemispheres, brain stem, and cerebellum (see FIG. 1). The cerebral hemispheres have the center controlling higher order mental functions, the cerebellum controls motor and balance functions, and the brain stem controls life support functions. Information related to feeling is processed in the hypothalamus in the brain stem upper portion, and in the limbic system including the brain called the limbic cortex existing deep in the cerebral hemispheres. The information processing of higher-order feeling involves the neocortex of the cerebral frontal lobe to a considerable extent. Control of alertness that affects the intensity of feeling involves the hypothalamus and a system called a reticular activating system existing in the brain stem. Activities relating to brain waves have a close relation with these systems. A recent report indicates that fluctuation of brain waves varies with changes in feeling or degree of alertness.

Feelings are always changing, and the time-course measurement of brain wave fluctuation is considered to be more suitable for examining emotional changes compared with the static approach to information processing as represented by evaluation of mean values in conventional practice.

Figure 2:
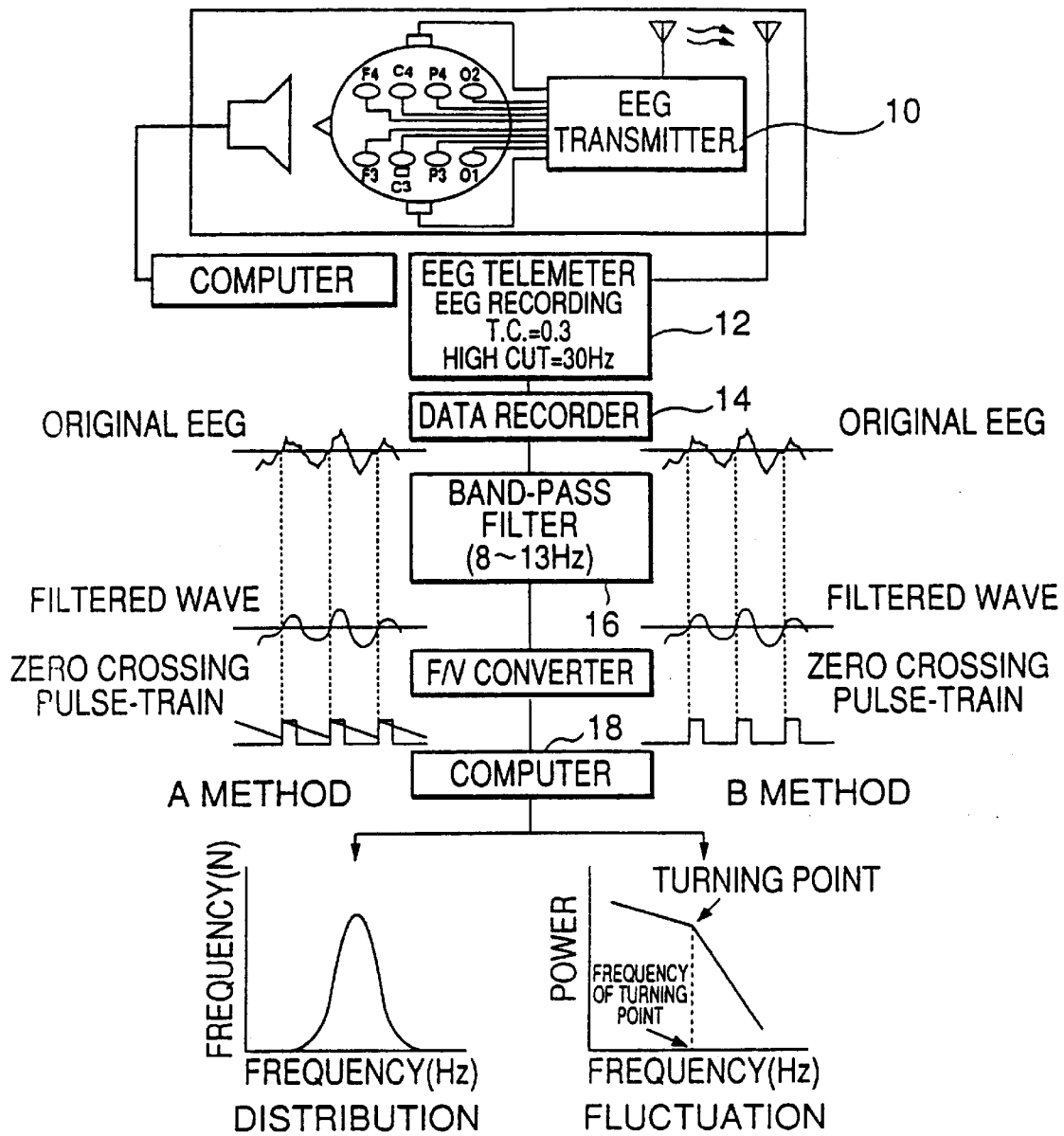
FIG. 2 shows the structure of an experimentation system in accordance with the invention.

This invention uses α-wave fluctuation in brain waves as an indicator. The α-wave frequency rhythm was observed under olfactory stimuli such as fragrance and odor, under audiovisual stimuli such as video image and sound, and under audio stimuli including natural and artificial sounds and low-frequency noise, and at the same time, psychological conditions were recorded and classified according to characteristics. Fluctuations in the α-wave frequency rhythm recorded were stored corresponding to classification. FIG. 2 shows the system configuration used for the experiment.

As a result of finding correspondence between α-wave fluctuation and subjective alertness or comfortableness, it was discovered that the characteristics of α-wave fluctuation change responded to changes in psychological conditions. The spectrum analysis of the characteristics of assorted fluctuations in the α-wave frequency indicates that the frequency fluctuation of α-waves exhibits a gentle rhythm (characteristic close to 1/f) during comfortable rest or a relaxing condition, whereas such characteristics collapse in uncomfortable conditions.

It is also possible to estimate alertness and comfortableness directly from EEG fluctuation characteristics without classifying psychological conditions. This method includes multiple regression analysis (or linear analysis) with fluctuation characteristics as the independent variable and the psychological response as the dependent variable. Alternatively, it may include preparation of an estimation algorithm using a neural network (for non-linear analysis). It was found that, by using these approaches, comfortableness was estimated from EEG fluctuation characteristics obtained from the frontal and central regions of the brain, and alertness was estimated from EEG fluctuation of the parietal and occipital regions of the brain with relatively high probability, details of which will be described below.

B-2. Detection and Analysis of the α-wave Frequency Fluctuation

Frequency fluctuation is measured using a system shown in FIG. 2.

(1) Measurement of Brain Waves

Brain waves comprise various complex frequency components in response to the conditions of the living body, and are continuously fluctuating. It is difficult to grasp the characteristics of brain waves by visual observation. One conventional technique for examining brain waves is to use a band pass filter to extract only a specific frequency component, which is then analyzed using a computer. In this invention, detection and analysis of fluctuation in brain waves is carried out using a experimental system shown in FIG. 2.

(2) Detection of Fluctuation Characteristics (i) Extraction of α-wave component

Brain waves are detected through 8 electrodes (F3, F4, C3, C4, P3, P4, O1, O2) put on the head of human subject, as seen from FIG. 2. The detected brain waves are transmitted by an EEG transmitter 10, and received at an EEG telemeter 12 which has a time constant of 0.3 second and has a high cut filter for cutting signals over 30 Hz. The frequency component through the EEG telemeter 12 is recorded by a data recorder 14. The EEG recording is passed through a band-pass filter 16 (8 to 13 Hz) to extract α-wave components. Although both amplitude and frequency fluctuations are observed in the extracted α-waves, focus is placed on frequency fluctuation in the embodiment only because amplitude shows significant differences among individuals. Of course, it is possible to focus on amplitude fluctuations and analyze them based on the system and apparatus of the invention.

Among the frequency components having passed through the band pass filter 16, only those having an amplitude greater than a given level are considered as α-waves. Even when appearing to be α-waves, the filtered waves are amplified as required, with reference to a level, in the case that the subjects have only relatively limited EEG amplitude overall.

(ii) Extraction of Frequency Fluctuation in α-wave (Zero-Crossing Method)

The datum line is set in the middle of the electric potential fluctuations of the filtered wave, and pulse having a given potential are generated each time the wave crosses the datum line in a given direction (e.g. from negative to positive).

There are two methods for extracting the pulse train as fluctuation. One method is to give a time constant to attenuation process of pulse potential and accumulate potential for every pulse. This method is referred to as method A. The other is to detect pulses successively using computer, and to calculate a time interval (cycle) for every consecutive pulse. The reciprocal of the resulting value is converted into the time series of instant frequency (i.e. frequency is 1/cycle). This is referred to as method B. In method A, frequency fluctuation is displaced by analogue potential fluctuation. In method B, when arranging the calculated frequency for every wave in the sampling order (in the order of elapsed time), frequency fluctuation in α-waves are extracted as a waveform consisting of points.

The forgoing processes are all computer-processible. However, the processes up to pulse generation and analogue output are preferably carried out outside the computer.

(3) Analysis of Fluctuation Characteristics

Based on the extracted EEG fluctuation data, fluctuation characteristics are analyzed.

(i) Histogram Method

This analysis is applicable to the data extracted by the above-mentioned method B. As preliminary processing, a specific frequency value in the α-wave frequency band is counted every 0.01 Hz to calculate frequency distribution. Then, the mode value and frequency (or average frequency) corresponding to the mode value are calculated in order to extract distribution characteristics.

(ii) Spectrum Method

This analysis is applicable to both method A and B. For the method A, the potential fluctuation is A/D converted by the computer at a given sampling frequency, and the digitalized data sequence is divided by a unit time. Based on the data in a unit time, power spectrum with respect to the fluctuation frequency is calculated via spectrum analysis by the FFT method.

For the method B, the time data recorded is divided into a number of unit times, and data are re-sampled at a constant time period within each unit time. Based on the unit data, a power level with respect to the fluctuation frequency is calculated via spectrum analysis using the FFT method. These processes are carried out because of the fact that spectrum analysis does not produce constant time intervals among plots of changes in α-wave frequency converted into instant frequency, and to avoid a time lag between calculated and true sample lengths. More particularly, instant frequency time series is produced from the obtained time data by the following processes.

Frequency Fm at a sampling period Sm is determined by the equation:

$$Fm = 1/\{P_{n+1} - \max(Pn)\}$$

under the condition of:

$$S_{n-1} < \max(Pn) \leq Sm \leq P_{n+1}$$

where the meaning of each of the letters is as follows.

Pn: generation time of the n-th pulse

S: sampling period m: ordinal number

Sm: the m-th sampling period (determined by SXm)

Fm: the m-th sampled frequency max(Pn): the maximum value of Pn till the sampling period Sm In this method, assuming that the sampling period is 50 ms (20 Hz), originally obtained time data are sampled without a sampling drop, and sample length (time interval) can be constant.

Then, from these time data, a tendency of changes in fluctuation spectrum with respect to fluctuation frequency is expressed in numerical values using the gradient of linear regression, so as to identify the characteristics of the changes. The fluctuation power value noticeably changes after passing over a certain frequency. After identifying that frequency over which the gradient changes (i.e. inflecting frequency), the frequency band is separated into two band widths with the boundary frequency, that is, low and high frequency band widths, each of which are regression-analyzed separately.

B-3. Psychological Evaluation Method for Alertness and Comfortableness

In psychology and psychophysiology, it is generally accepted that the psychological approach is mainly based on two pivotal parameters, comfortableness and alertness, as representing the emotional condition of individuals. It is preferable for the measurement of comfortableness to set these parameters as a common and basic item and to select additional evaluation items depending on stimulations.

Psychological methods for evaluating comfortableness also include the rating scale method, the semantic differential (SD) method, and analogue scale method, among which it is known that the analogue scale method is the most suitable for evaluating feeling.

In evaluation of the psychological condition of the subjects with the aid of the evaluation table, it is preferable to make an assessment before and after the physiological measurement, during both rest and experimental conditions, to observe and review changes in psychological conditions as depicted by two sets of measurements.

B-4. Synthesis of the Result of Processing

Spectrum information calculated for each individual is related to the psychologically evaluated values of comfortableness and alertness to find correspondence between the values of fluctuation characteristics and psychological conditions.

Although it is known that the frequency fluctuation characteristics of the α-waves are correlated to comfortableness and alertness, no effective and accurate method has yet been established for determining correspondence between these factors quantitatively.

The present invention uses NN (neural network) templates capable of extracting characteristic components from multifaceted and non-linear data, and classifying complicated information, to reveal an algorithm which can quantitatively estimate comfortableness and alertness with high precision. The following are preferred examples for embodying this invention.

C. PREPARATION OF NEURAL NETWORK TO ESTIMATE ALERTNESS AND COMFORTABLENESS

In the preferred embodiment, NN templates are prepared to estimate alertness and comfortableness from fluctuation in brain waves via learning, based on data obtained from the physiological and psychological experiments having been described above.

C-1. Experimental Data

In order to prepare NN templates for estimating alertness and comfortableness, it is necessary to obtain experimental data used for the learning of NN templates. FIG. 3 shows the construction of such experimental data used for training NN templates.

Data were obtained from the experimental system shown in FIG. 2, which include brain waves of each subject (8 channels of F3, F4, C3, C4, P3, P4, O1, and O2) and corresponding psychological evaluation scores (as to comfortableness and alertness). The values of 8 channels of brain waves and the corresponding psychological scores are grouped into a set, and the experimental data consisted of total of 1200 sets. These data were statistically analyzed (for linear approximation). FIG. 10 presents correlations between the evaluation factors. Correlation between individual fluctuation of brain waves for each channel for alertness and comfortableness is indistinctive (although it is statistically significant), which implies that it is difficult to estimate alertness and comfortableness from brain waves using the conventional statistical method.

C-2. NN template configuration

Figure 5A:
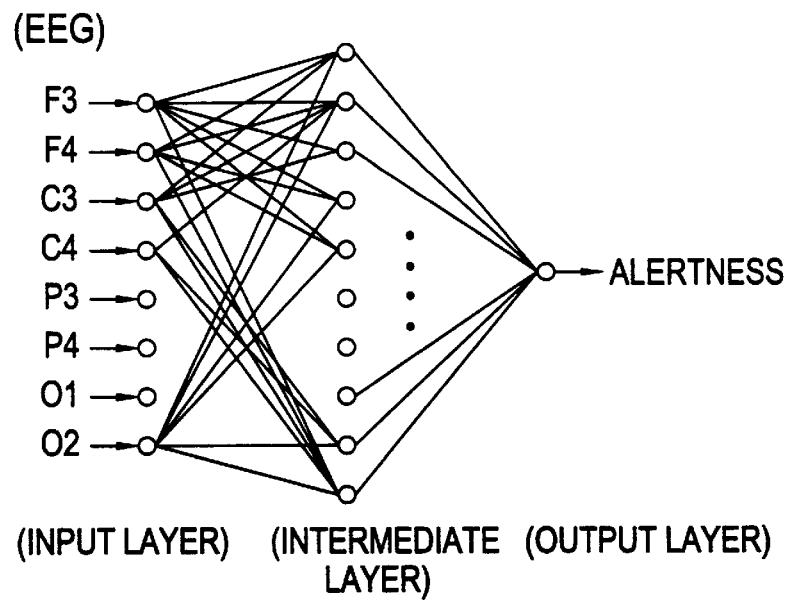
FIG. 5A shows an NN template configuration for estimating degree of alertness based on brain wave fluctuations.
Figure 5B:
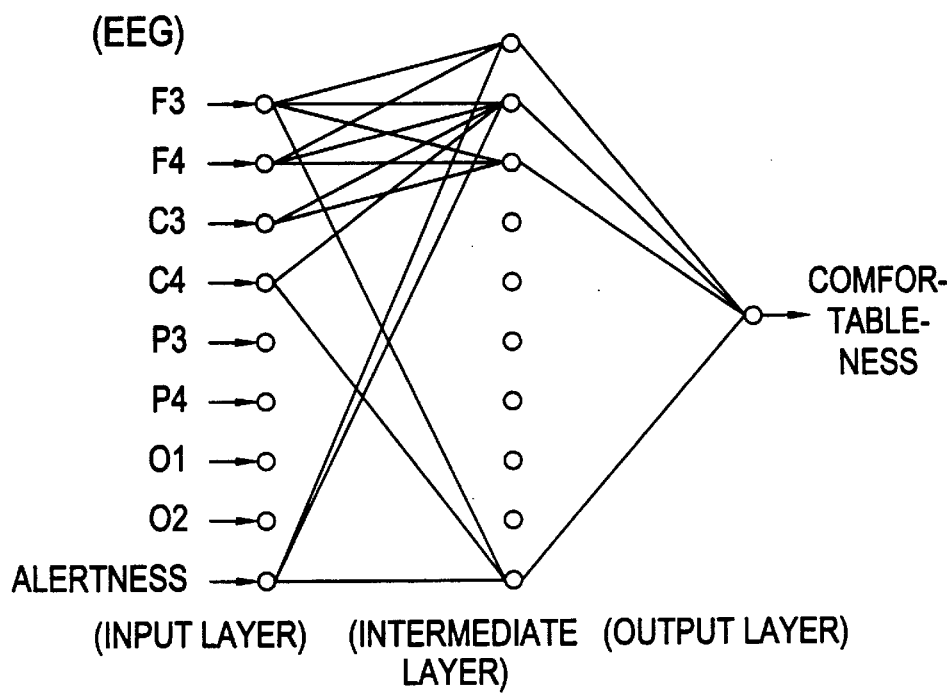
FIG. 5B shows an NN template configuration for estimating comfortableness based on brain wave fluctuations and alertness.
Figure 6A:
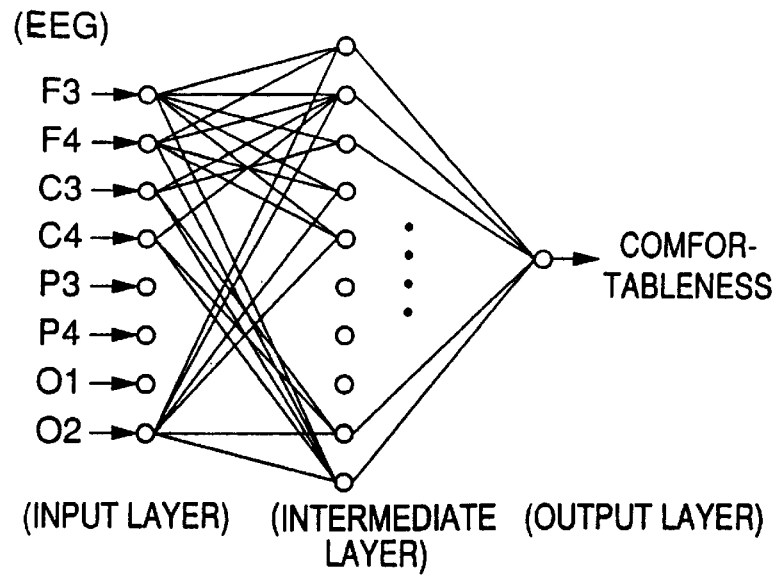
FIG. 6A shows an NN template configuration for estimating comfortableness based on brain wave fluctuations.
Figure 6B:
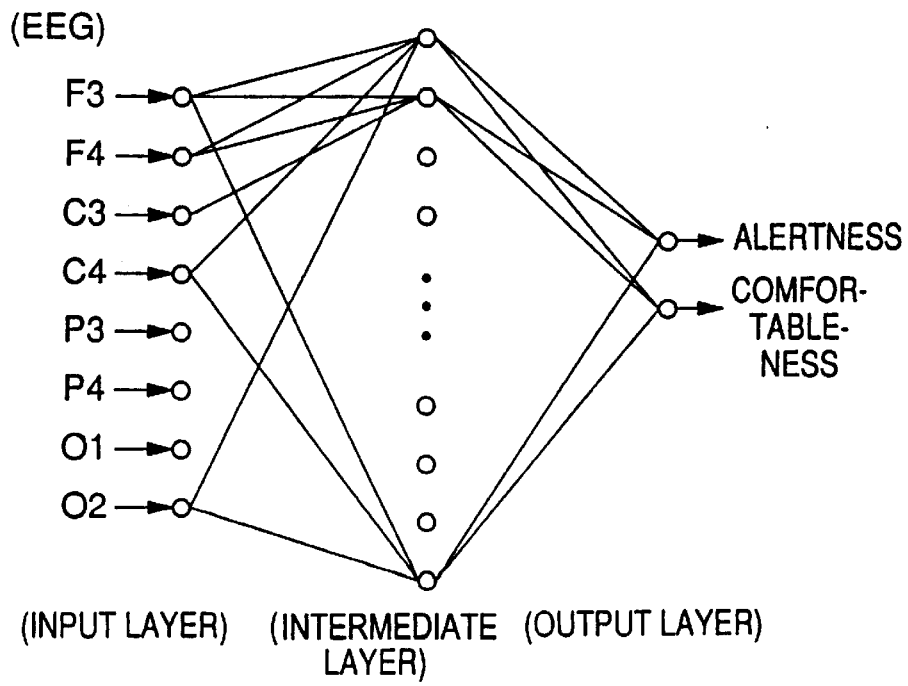
FIG. 6B shows an template configuration for estimating alertness plus comfortableness based on brain wave fluctuation.
Figure 7A:
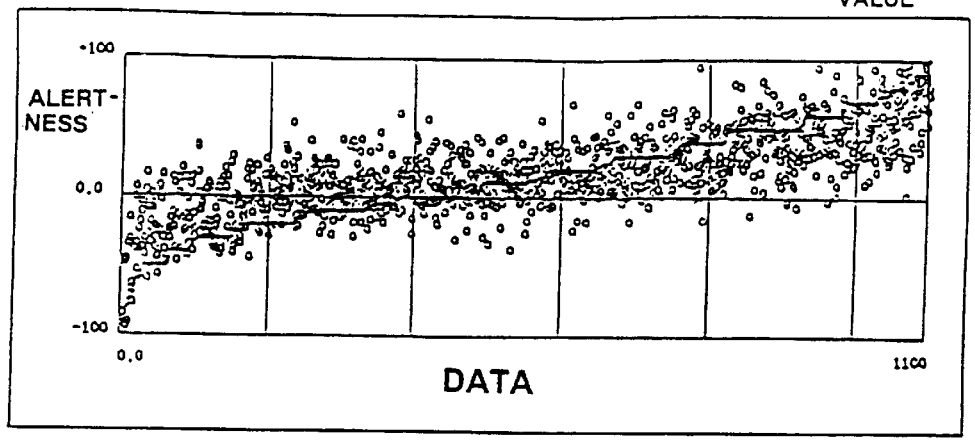
FIG. 7A is a graph showing a relationship between training data and NN estimated values based on experimental data of the alertness-estimating neural network, where the number of neurons in the intermediate layer is 35.
Figure 7B:
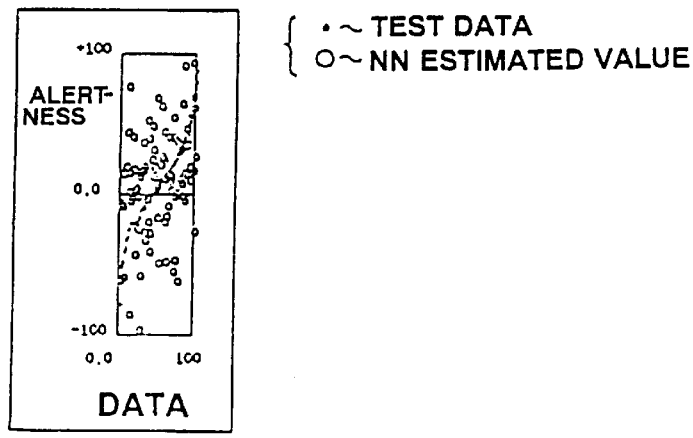
FIG. 7B is a graph showing a relationship between test data and NN estimated values based on experimentation data of the alertness-estimating neural network, where the number of neurons in the intermediate layer is 35.
Figure 8A:
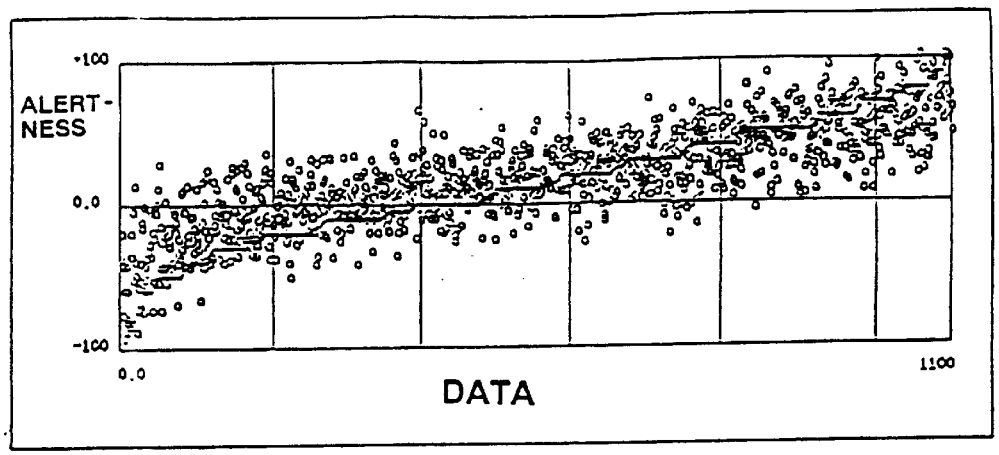
FIG. 8A is a graph showing a relationship between training data and NN estimated values based on experimental data of the alertness-estimating neural network, where the number of neurons in the intermediate layer is 70.
Figure 8B:
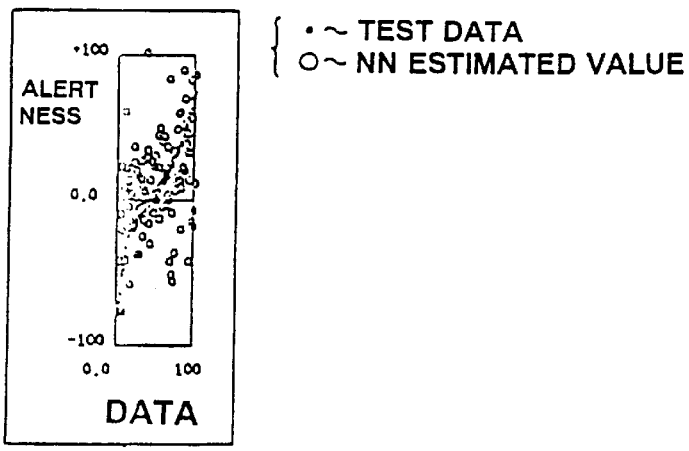
FIG. 8B is a graph showing a relationship between test data and NN estimated values based on experimental data of the alertness-estimating neural network, where the number of neurons in the intermediate layer is 70.

Configurations of NN for estimating alertness and comfortableness are shown in FIGS. 5A, 5B, 6A and 6B. The inventors found that alertness and comfortableness are not independent from each other, but the comfortableness is dependent on alertness (i.e. alertness affects comfortableness). The NN template shown in FIG. 5A is suitable for estimating of alertness. Similarly, the NN template of FIG. 6A which estimates comfortableness directly from fluctuation in brain waves and the NN template of FIG. 6B which outputs alertness and comfortableness at the same level are not sufficient for accurately estimating comfortableness. Instead, the NN template shown in FIG. 5B is much more accurate, which estimates comfortableness from both fluctuation in brain waves and alertness.

Figure 4:
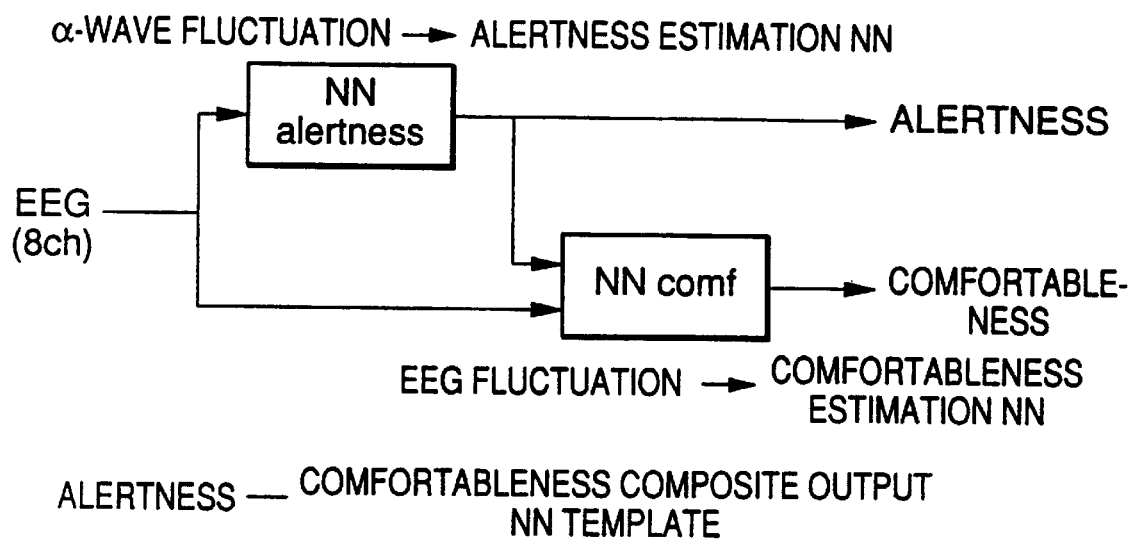
FIG. 4 shows an NN template configuration having a composite output of alertness and comfortableness.

In view of the above, the NN template for estimating comfortableness based on both α-wave fluctuation and alertness is constructed as a cascade structure shown in FIG. 4 (NN template having composite output of alertness and comfortableness). The input circuit layer of the alertness estimation template ($NN_{alertness}$) consists of 8 units representing the α-wave fluctuation coefficients (8 channels of F3, F4, C3, C4, P3, P4, O1, and O2), while the output circuit layer consists of a single unit representing alertness, as is shown in FIG. 5A.

On the other hand, the input circuit layer of the comfortableness estimation template ($NN_{conf}$) consists of 9 units representing α-wave fluctuation coefficients (8 channels) and alertness, while the output layer consists of a single unit representing comfortableness (FIG. 5B).

D. SIMULATION EXPERIMENT AND RESULTS

The preparation of NN templates for estimating alertness (FIG. 5A) and comfortableness (FIG. 5B) was simulated. The NN interior structure after training, particularly the coupling strength between the input and output layers, was examined so as to observe the extent of the effect of each input on the output.

D-1. Experimental Result of Alertness Estimation NN

For the NN template for estimating alertness in FIG. 5A, fitting to 1100 training data and 100 test data was simulated, varying the number of hidden units (intermediate layers) and the number of training actions. First, the neural network was trained with learning data, then alertness was estimated from α-wave fluctuation using the trained NN template. Fitting to the training data and test data was observed, the results of which are shown in FIGS. 7A, 7B, 8A and 8B. The experimental conditions applied were shown in FIG. 11.

The coupling strength between input and output layers in the respect cases was obtained to review the extent of the effect of input on output. The result is shown in FIG. 11 in the column of "dominant portion (where input significantly affects output)".

The extent of the effect was indicated with the correlation coefficient obtained from the coupling strength between each input (each channel of brain waves) and output (alertness). In other words, it is indicated as a value of coupling strength between each input and output (alertness) divided by total coupling strength.

D-2. Experimental Results of Comfortableness Estimation NN

Figure 9A:
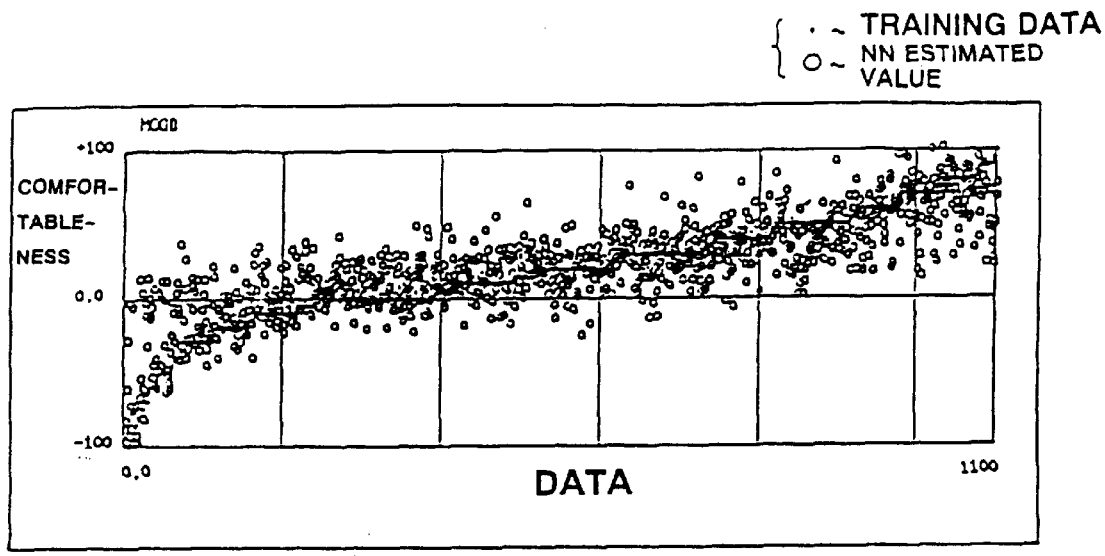
FIG. 9A is a graph showing a relationship between training data and NN estimated values based on preliminary experiment data of the comfortableness-estimating neural network.
Figure 9B:
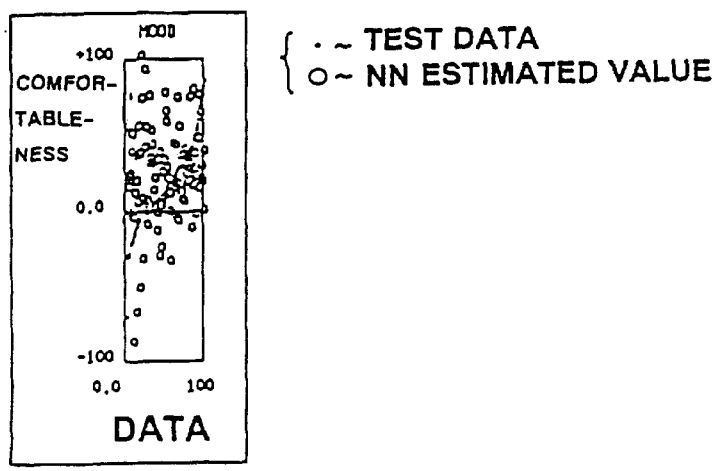
FIG. 9B is a graph showing a relationship between test data and NN estimated values based on preliminary experimentation data of the comfortableness-estimating neural network.

For the NN template for estimating comfortableness in FIG. 5B, fitting to training data was preliminarily simulated in the same manner as the alertness estimation template. The result is shown in FIGS. 9A and 9B, and the experimental conditions, as well as the correlation between input and output, is in FIG. 12.

In all simulations, the training rate coefficient, epsilon, was 0.01, the inertia term 0.9, and a three-layer sigmoid structure was used.

From the above-mentioned simulations, the following advantages are understood.

The optimum numbers of hidden units (intermediate layers) and training actions improve the accuracy, as well as fitting ability to test data, of the alertness estimation NN template, which realizes a practical method for estimating psychological data.

The comfortableness estimation NN template is also improved by estimating comfortableness from both α-wave fluctuation and alertness, as well as by the optimum numbers of hidden units and training actions.

It is generally known (as an empirical law) that good results of alertness measurement can be obtained from brain waves of the parietal region of the brain, and that brain waves of the frontal region are effective for measurement of comfortableness. The experimental results using NN templates in accordance with the invention quantitatively analyzed and proved this theory.

E. HOURGLASS TYPE OF NEURAL NETWORK

In the above-described example, an algorithm is produced for estimating psychological parameters (alertness and comfortableness) from a physiological parameter (EEG fluctuation), by using neural networks.

Training of the neural network is conducted by reversely propagating error signals from the output to the input side so as to minimize the sum of squares of differences between the network output and teacher signal (this procedure is called back propagation), thereby varying the synaptic coupling weight between the first and second layers of the network and between the second and third. The teacher signal is obtained, in this example, by an inquiry survey (questionnaire).

However, psychological evaluations used as teacher signals are based on an inquiry survey, and it generally contains a wide range of errors. This is due to dispersion of data caused by differences among individuals and experimental conditions. Thus, positively using questionnaire results as teacher signals involves problems.

Normally, the questionnaire method is used to measure alertness and comfortableness during clinical psychological examination. However, correct results can be expected only when the subjects have the capability of correctly understanding the meaning of the questions and correctly judging themselves when they answer honestly and without any pretension. It is very probable that psychological evaluation data (such as alertness or comfortableness) contain inconsistencies. In addition, the psychological evaluation of alertness and comfortableness measured by the questionnaire method has the disadvantage that the parameters are limited to manifest characteristics recognizable in the subjects consciousness.

Comfortableness is mostly recognizable, and there is not so big difference between the actual comfortableness of the subject and psychological evaluation obtained by a questionnaire. On the other hand, alertness or degree of fatigue is often non-recognizable, and it should be expected that there is a relatively big difference between the actual condition of the subject and evaluation based on the questionnaire.

In order to obviate such an adverse effect, it is preferable to use a neural network which is capable of learning, rather than using psychological evaluations as main parameters. One example of such a neural network is hourglass type of neural network.

The hourglass type of NN has been used in the field of telecommunications for compression and decompression of information. It has also been applied to the study of human senses in recent years. "Neural Network Model For Recognizing Shape Of a Grasped Object and Decides Hand Configuration" by Fukumura et al, Japan, IEICE, Technical Report, NC90-104, 1991-03, proposed an integrated model of different kinds of information (visual sense and somatic sense) for motor control of human arms. "Neural Network Model For Acquiring an Internal Representation Of the Weight Of Grasped Objects" by Uno et al. Trans. IEICE D-2, J76-D-2, 3, pp663–671, 1993-03, discloses a technique for estimating the weight of an unknown object to be gripped as an internal expression in the middle layer of the neural network. For instance, when a man holds an object in his hand and moves his arm, a dynamics system of the whole arm varies in accordance with the weight of the object, and tension of the arm muscle must be changed. But in reality, a man can appropriately move his arm in accordance with the weight of the object, although he does not actually know the exact weight of the object. This is considered to be because internal expression of the weight of the object has been obtained in the motor center through experience.

Figure 13:
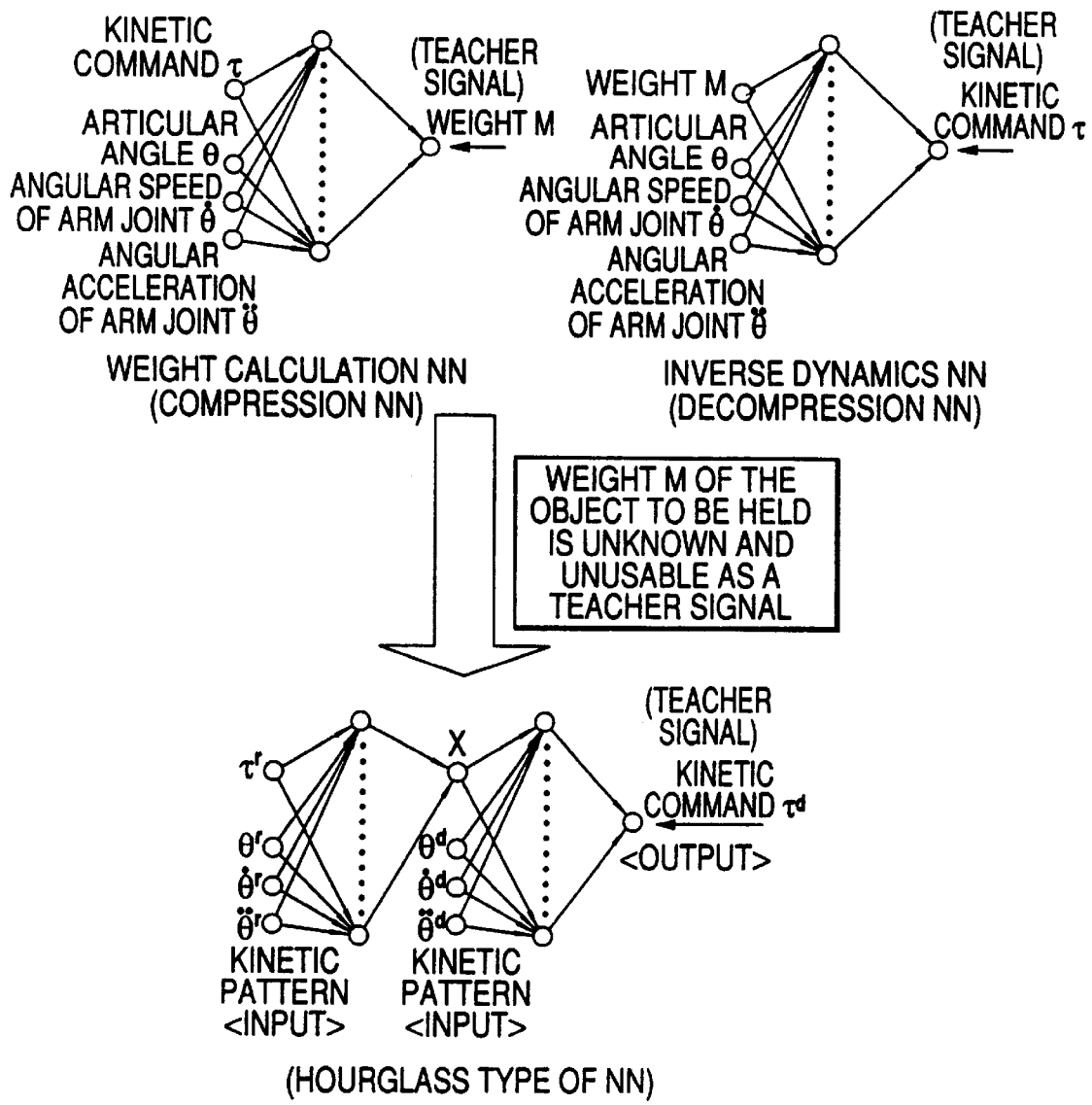
FIG. 13 shows a structure of an hourglass type of neural network.

The above-mentioned publication of Uno et al. proposes a neural circuit model for obtaining internal expressions of the weight of the object to be held, using observable data of articular (joint) angle representing a arm position and its driving torque. The basic idea of this technique is to construct a multi-layered neural network work model by combining a network for calculating a weight of the object to be held, based on the articular angle of the arm and its torque, with an inverse dynamics network for calculating a torque based on the weight of the object to be held and the articular angle of the arm. This structure is shown in FIG. 13. It is described in this publication that this structure enables the network to learn the movement of the arm without positively (mainly) using the weight of the object to be held. After sufficient learning (training), the active value of the neurons in the intermediate layer becomes a monotonic function of solely the weight of the object to be held, without depending on the arm position. Namely, an internal expression corresponding to the weight of the object has been established in the neural network.

By supplying only a kinetic pattern and kinetic command as teacher signals to the neural network, the internal expression corresponding to the weight is obtained as an activity value in the intermediate layer of the neural network. In order to indicate the weight as an internal expression, it is preferable that the number of neurons in the intermediate layer is smaller than that in the other layers. This type of network is a so-called hourglass type of neural network.

Figures 14A, 14B:
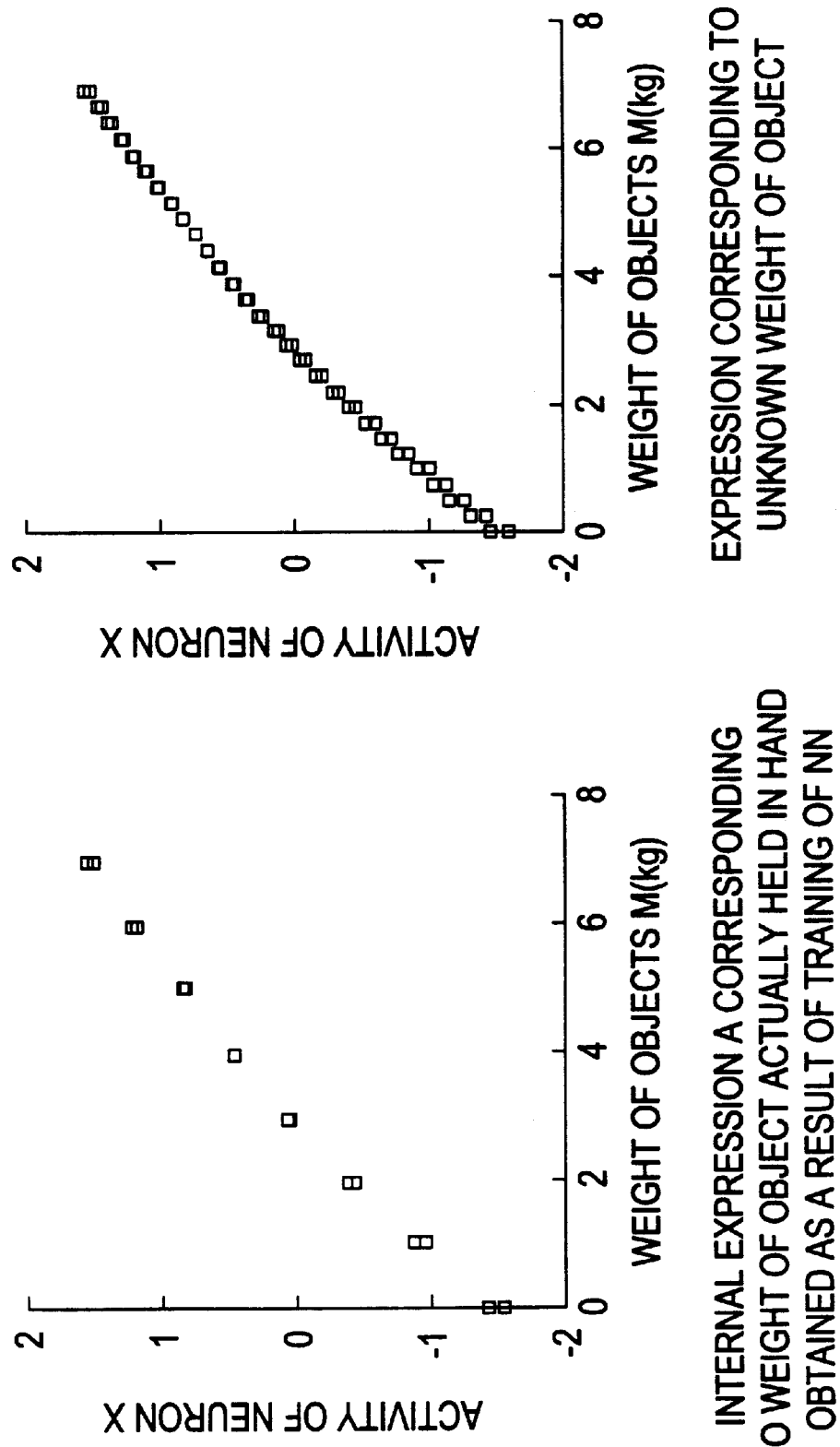
FIGS. 14A and 14B show graphs plotting weight of objects vs. activity of neurons obtained as an internal expression in the intermediate layer of the hourglass type of neural network of FIG. 13.

FIGS. 14A and 14B shows a relationship between the weight of the object to be held in the hand and the activity value of the neuron in the intermediate layer (shown by the letter "X" in FIG. 13). The horizontal axis represents actual weight of the object held in the hand, which is unknown by the subject, and the vertical axis represents activity of the neuron X. The left graph plots activity values of the neuron with respect to the actual load values obtained as a result of experiment, and the right graph shows internal expressions for non-learning data. As is seen from the graph, the activity of the neuron X belonging to the intermediate layer is a monotonic function of the weight, and it is understood that an internal expression corresponding to the weight has been established in the neural network.

When applying the hourglass type of neural network to the present invention, the network comprises a combination of a data compression neural network for calculating a psychological evaluation value such as alertness and comfortableness from EEG fluctuation and a decompression (inverse) network for calculating EEG fluctuation from the psychological evaluation value, which constructs an hourglass type of multi-layered neural network model having a small number of neurons in its intermediate layer. In this structure, it is possible to obtain internal expressions corresponding to alertness or comfortableness in the network without directly using the psychological evaluation values for training of the network. In this case, the psychological evaluations are indirectly used to determined which neuron in the intermediate layer of the neural network after learning corresponds to alertness or comfortableness. The hourglass type of neural network realizes accurate estimation of alertness and comfortableness from EEG fluctuation.

Figure 15:
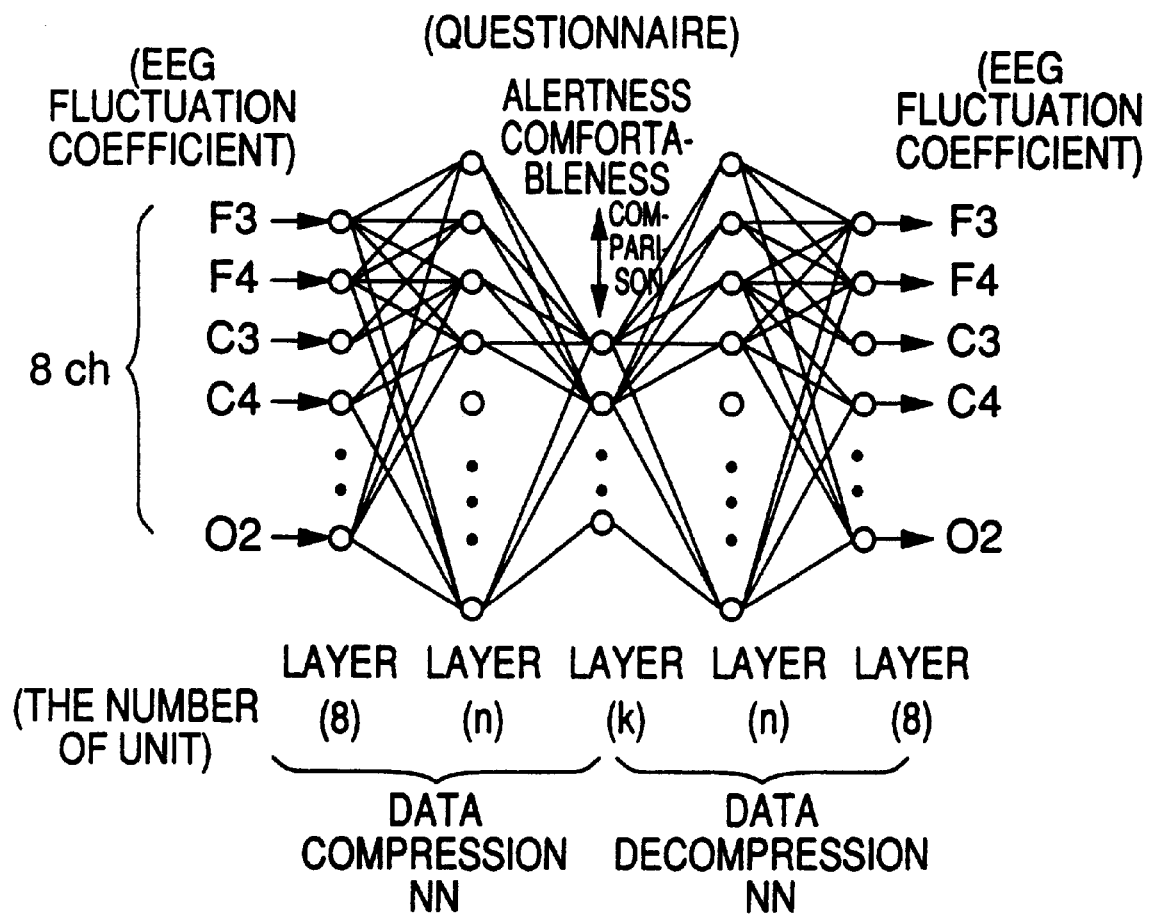
FIG. 15 shows a detailed structure of the hourglass type of neural network.

FIG. 15 shows a structural example of an hourglass type neural network used in the invention for estimating alertness and comfortableness from the EEG fluctuation. The hourglass type neural network comprises a three-layered data compression NN and a decompression NN, which are combined symmetrically. Inputs and outputs are units of physiological parameters (8 channels of EEG fluctuation coefficients) which are the same as the EEG fluctuation signals used in the neural network shown in FIG. 5.

The training of this neural network is carried out by backwardly propagating a difference signal between an output of the NN and a teacher signal (back propagation), from an output side to an input side, so as to minimize an addition of output of the NN and a square of the difference between the teacher signal and the actual output, and by varying the coupling load (weight) of synaptic coupling between the first and second layers, between second and third layers, between third and fourth layers, and between fourth and fifth layers. The feature of the present invention is that both the output signal and teacher signal used for training the neural network are 8 channels of EEG fluctuation coefficients. By giving the EEG fluctuation coefficients to both the teacher signal and input signal for the learning of the neural network, neurons corresponding to the degree of alertness and comfortableness are formed in the intermediate layers. Thus, internal expression of alertness and comfortableness are obtained in the third layer of the neural network.

The first and fifth layers of the neural network comprise 8 units (neurons) corresponding to 8 channels of EEG fluctuation coefficients. The second and fourth layers consist of 70 to 90 neurons. Logically, the third layer must have at least 2 neurons to obtain internal expressions of alertness and comfortableness, but it actually needs more neurons. The number of neurons in the third layer is set so as to allow the psychological evaluation to appear as a constant pattern. This actually depend on the EEG fluctuation coefficient data used for training the neural network, and an appropriate number of neurons should be selected through experiment action.

The obtained internal expressions can be confirmed by comparing each output of the the third layer, which has been obtained by inputting the EEG fluctuation, with the psychological evaluation value (degree of alertness and comfortableness), which has been obtained from the questionnaire. Thus, the psychological evaluation values such as alertness or comfortableness obtained from the questionnaire are not directly used for training the neural network, but are used for reviewing which internal expression corresponds to which psychological parameter. The internal expression of the psychological condition may be obtained as a single output value of the third layer of the neural network (shown in FIG. 15) for some cases, or alternatively it may be obtained as a constant output pattern of the whole units for other cases. The publication by Fukumura et al. mentioned above shows that the activity pattern of the neurons in the intermediate layer varies depending on the shape of the object to be held, for example, a cylindrical, cubic, or spherical shape.

The graph in FIG. 16A shows a correlation between the output values of the first unit of the third layer and the alertness obtained from the questionnaire, while the graph in FIG. 16B shows a correlation between the output values of the second unit of the third layer and the comfortableness obtained from the questionnaire. The horizontal axis represents psychological evaluation obtained from the questionnaire, and the vertical axis represents actual output value of the third layer. In this example, the first unit of the third layer is used for outputting degree of alertness and the second unit is used for outputting degree of comfortableness.

In these graphs, the output of a certain unit of the third layer is obtained as a result of inputting various patterns of the EEG fluctuation coefficients into the trained hourglass type neural network. As can be seen from the graphs, the output of the first and second units of the third layer have a highly correlated relation with the questionnaire result of alertness and comfortableness, respectively. In other words, the internal expressions corresponding to alertness and comfortableness are obtained in the first and second units, respectively.

Since the training of the neural network is carried out using only a physiological parameter (EEG fluctuation signal), the degree of alertness or comfortableness obtained in each unit of the third layer does not contain the variation (dispersion) in psychological evaluation from the questionnaire. In this regard, the hourglass type neural network is capable of more accurate estimation compared with the simple three-layered neural network described in the above subsections A–E.

In FIG. 16, it seems that the estimation values of alertness and comfortableness obtained by the hourglass type neural network are not consistent with the questionnaire evaluations and that they indicate variation. However, this variation is caused by the problems of the questionnaire method.

The simple three-layered neural network directly utilizes psychological evaluation values as teacher signals for training the neural network. The resultant psychological conditions estimated by such a neural network are limited to recognizable psychological conditions (such as comfortableness) of which the subject can be conscious. On the other hand, the hourglass type neural network does not directly utilize the psychological evaluations as teacher signals, and is capable of estimating such psychological conditions that are difficult for the subject to recognize (alertness or degree of fatigue).

Although it has been described in the above-mentioned examples that psychological evaluations obtained by the questionnaire are used as parameters of alertness, work results of selective reaction tests may be used as parameters instead of the psychological evaluation. In this case, the EEG fluctuation coefficients during the selective reaction test and the work results are measured, and the neural network is trained based on these data. Alertness and the degree of fatigue are estimated from the EEG fluctuation during actual working, by the thus trained neural network.

It is known that the work results of the selective reaction tests reflect the degrees of alertness and comfortableness rather than the psychological evaluations. However, it is difficult to simultaneously carry out such test during the actual working. For example, it is almost impossible to perform selective reaction testing during the actual driving of the car. For this reason, psychological evaluations, which are measurable during actual working, have been used for real time measurement of the degree of alertness or fatigue, instead of the real-time work results.

In the present invention, the work result, which is difficult to correct during the actual working, is substituted by the EEG fluctuation as a physical parameter. This may achieve the same accuracy of real-time estimation of alertness or degree of fatigue as using work results. By making the neural network previously learn the relation between the work result and the EEG fluctuation, good estimation of alertness or degree of fatigue can be obtained by such a neural network.

FIG. 17 shows this method, that is, making the neural network learn the relation between the EEG fluctuation and work result and estimating alertness or degree of fatigue using the trained neural network. In the conventional method, psychological evaluations are obtained from the questionnaire during the actual driving because it is difficult to carry out selective reaction test simultaneously with driving action. This psychological evaluation and the corresponding EEG fluctuation are used as preliminary test data for learning of the environment. Then, alertness or degree of fatigue is estimated from the EEG fluctuation during the actual driving. On the contrary, in the present invention, the neural network previously learns the relation between the EEG fluctuation obtained during the experiment (e.g. selective reaction test) and alertness or degree of fatigue, using work results, and then estimates alertness or degree of fatigue during the actual driving.

By using working results which are considered to be more closely associated with alertness, rather than psychological evaluation using the questionnaire, the accurate analysis of information relating to physical and psychological conditions can be achieved by the vital information analyzing apparatus of the present invention.

For obtaining working results, Uchida-Kraepelin's test can be used, as well as selective reaction tests, and various known tests can be applicable to the present invention.

As a conclusion, the neural network used in this invention can estimate psychological conditions including alertness and comfortableness based on the input EEG fluctuation signals.

When combining two neural networks for estimating alertness and comfortableness, respectively, more accurate estimation can be achieved because comfortableness is estimated taking the first estimated alertness into consideration.

When using an hourglass type neural network, the training of the neural network is carried out using the EEG fluctuation signals and internal expressions corresponding psychological conditions can be obtained in the intermediate layer of the neural network without directly using the questionnaire evaluation.

Those skilled in the art can make many substitutions or modifications of the embodiments described above, without departing from the scope and spirit of the appended claims.

What is claimed is:

1. An apparatus for analyzing information relating to physiological and psychological conditions comprising a neural network receiving a physiological fluctuation signal as an input and estimating psychological conditions based on frequency variations of the physiological fluctuation signal.

2. The apparatus according to claim 1, wherein said neural network receives a pre-processed EEG fluctuation signal as a physiological fluctuation signal.

3. The apparatus according to claim 2, wherein said neural network estimates alertness as a psychological condition.

4. The apparatus according to claim 2, wherein said neural network estimates comfortableness as a psychological condition.

5. The apparatus according to claim 2, wherein said neural network comprises:

a first neural network receiving the EEG fluctuation signal as an input and estimating a degree of alertness; and a second neural network receiving the degree of alertness estimated by the first neural network and the EEG fluctuation signal as inputs and estimating comfortableness, thereby estimating both alertness and comfortableness as psychological conditions.

6. The apparatus according to claim 5, wherein said first and second neural networks are hourglass type neural networks, the EEG fluctuation signals are supplied to both input and output of each of the neural networks for training the neural networks, and output values of intermediate layers of the neural network represent the psychological conditions.

7. The apparatus according to claim 1, wherein said neural network is an hourglass type neural network, training of the hourglass type neural network is carried out by supplying the EEG fluctuation signals to both input and output, and output values of the intermediate layer of the neural network represents psychological conditions.

8. A method for analyzing information relating to physiological and psychological conditions, comprising the steps of:

inputting a physiological fluctuation signal; and applying the physiological fluctuation signal to a neural network to let the neural network estimate psychological conditions based on frequency variations of the physiological fluctuation signal.

9. The method according to claim 8, wherein said physiological fluctuation signal includes a pre-processed EEG fluctuation signal.

10. The method according to claim 9, wherein said psychological conditions include alertness.

11. The method according to claim 9, wherein said psychological conditions include comfortableness.

12. The method according to claim 9, wherein said psychological condition estimating step includes the steps of:

applying the EEG fluctuation signal to an alertness estimation neural network to estimate alertness; and applying the estimated alertness and the EEG fluctuation signal to a comfortableness estimation neural network, thereby estimating both alertness and comfortableness as the psychological conditions.

13. The method according to claim 12, wherein the alertness estimation neural network and the comfortableness estimation neural network are hourglass type neural networks, both of which have been trained with the EEG fluctuation signals at both input and output, and the output values of an intermediate layer of each neural network represent the psychological conditions.

14. The method according to claim 8, wherein the neural network used during application of the physiological fluctuation signal is an hourglass type neural network which has been trained with the EEG fluctuation signals at both input and output, and output values of an intermediate layer of the neural network represent the psychological conditions.

* * * * *